(12) United States Patent
Weigand et al.

(10) Patent No.: US 7,628,488 B2
(45) Date of Patent: Dec. 8, 2009

(54) METHOD FOR REPRODUCING A FIXATION MARK FOR OPHTHALMOLOGICAL THERAPEUTIC EQUIPMENT

(75) Inventors: Heino Weigand, Jena (DE); Carsten Lang, Bad Koestritz (DE); Markus Sticker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 10/595,846

(22) PCT Filed: Dec. 2, 2004

(86) PCT No.: PCT/EP2004/013675

§ 371 (c)(1),
(2), (4) Date: May 16, 2006

(87) PCT Pub. No.: WO2005/058215

PCT Pub. Date: Jun. 30, 2005

(65) Prior Publication Data

US 2007/0002278 A1    Jan. 4, 2007

(30) Foreign Application Priority Data

Dec. 12, 2003    (DE) ................................ 103 59 239

(51) Int. Cl.
*A61B 3/10* (2006.01)
(52) U.S. Cl. ...................... 351/211; 351/205
(58) Field of Classification Search ......... 351/237–239, 351/211, 205, 243
See application file for complete search history.

(56) References Cited

U.S. PATENT DOCUMENTS

| 2,238,207 | A | * | 4/1941 | Ames, Jr. et al. ............ 351/211 |
| 3,984,156 | A | * | 10/1976 | Jernigan ..................... 351/209 |
| 4,995,717 | A | | 2/1991 | Damato |
| 5,206,671 | A | * | 4/1993 | Eydelman et al. ........... 351/203 |
| 5,565,949 | A | | 10/1996 | Kasha, Jr. |
| 5,883,692 | A | | 3/1999 | Agonis et al. |
| 5,947,955 | A | | 9/1999 | Kadambi et al. |
| 6,238,385 | B1 | * | 5/2001 | Harino et al. .................. 606/4 |
| 6,474,817 | B1 | * | 11/2002 | McKinnon et al. .......... 351/243 |
| 2003/0160943 | A1 | * | 8/2003 | Xie et al. ..................... 351/209 |
| 2004/0046934 | A1 | * | 3/2004 | Sponsel et al. .............. 351/200 |
| 2006/0200013 | A1 | * | 9/2006 | Smith et al. ................. 600/319 |

FOREIGN PATENT DOCUMENTS

| DE | 31 43 882 | 9/1982 |
| DE | 41 08 403 | 10/1991 |
| DE | 41 08 435 | 10/1991 |
| EP | 0 882 438 | 12/1998 |
| JP | 7-148179 | 6/1995 |

\* cited by examiner

*Primary Examiner*—Jordan M. Schwartz
*Assistant Examiner*—James C Jones
(74) *Attorney, Agent, or Firm*—Reed Smith LLP

(57) ABSTRACT

The present invention is directed to a fixation mark which is to be displayed to the patient in order to prevent unwanted eye movements during the treatment of an eye without taxing the patient's ability to concentrate. In the method according to the invention, the fixation mark which is to be displayed and on which the patient must orient the eye to be treated by foveal focusing is projected in the field of vision of the eye to be treated. To prevent unwanted eye movements, the fixation mark is moved in the field of vision of the patient. The movement is carried out in such a way that the patient can easily follow the fixation mark. The proposed technical solution relates to a fixation object which can be used in ophthalmologic examination devices as well as in ophthalmologic treatment devices. Since the patient is occupied in following the fixation object with his/her eyes, the risk of glancing away is substantially reduced. In this way, unwanted and uncontrolled movements of the eye being treated can be minimized.

9 Claims, No Drawings

METHOD FOR REPRODUCING A FIXATION MARK FOR OPHTHALMOLOGICAL THERAPEUTIC EQUIPMENT

CROSS-REFERENCE TO RELATED APPLICATIONS

This application claims priority of International Application No. PCT/EP2004/013675, filed Dec. 2, 2004 and German Application No. 103 59 239.3, filed Dec. 12, 2003, the complete disclosures of which are hereby incorporated by reference.

BACKGROUND OF THE INVENTION a) Field of the Invention

The present invention is directed to a fixation mark that is presented to the patient to prevent unwanted eye movements during the treatment of an eye without taxing the patient's ability to concentrate.

b) Description of the Related Art

While the use of moving fixation marks in ophthalmologic devices is already known, this primarily relates to the determination of the visual field by means of perimetric arrangements and not to the suppression of unwanted eye movements while looking at a rigid fixation object during examination or treatment.

For example, DE 31 43 882 describes a method for ensuring fixation in ophthalmologic examination devices, particularly for determining the visual field. A fixation point is projected on a surface lying in the viewing direction of the patient and is coupled with a marking point to correlate its relative position with the visual field pattern to be established. The fixation point is periodically moved slowly on a predetermined path so that the patient can easily follow this movement. The path of the fixation point can be a straight line, an elongated ellipse, or a circular path. Excursion is advantageously +/−2° in horizontal direction and +/−0.2° in vertical direction with an excursion rate of about 2° per second. The instantaneous relative position of the fixation point with respect to the test mark can be transferred into the visual field model optically and electronically. Depending on the type of perimetric hemisphere that is used, the projection of the fixation point and test mark can be carried out through front projection or back projection.

A perimeter, particularly a hemispherical perimeter with a reflex fixation safeguard, is described in DE 41 08 403. In this case also, the visual field is analyzed by means of a fixation mark that is moved periodically relative to the patient. However, the movement is carried out by periodically rotating the hemispherical perimeter, together with the fixation mark which is rigidly connected to it, around an imaginary vertical axis substantially extending through the eye to be examined. The approximately circular light spot which can be deflected by two angular degrees can be projected on selected positions of the inner surface of the hemisphere by known electrically controllable systems. It is not described in detail how the visual field is determined from the results of the examination.

The solution described in U.S. Pat. No. 4,995,717 is also directed to a device for determining the visual field of a patient. For this purpose, a reference mark is placed in the center of a computer display on which the patient's eye must be fixated. Light marks are then generated successively on the computer display to determine the visual field of the patient. The patient signals, e.g., by actuating a mouse, when he/she can see the light mark as it becomes visible. The visual field and any defects of the eye being examined are determined by evaluating the detected light marks.

In contrast to the references mentioned thus far, DE 41 08 435 describes an arrangement for monitoring fixation which can preferably likewise be applied for devices for examination of the visual field, but principally also for other ophthalmologic instruments. Means are provided for rotating a structured fixation mark around a central axis to furnish a functional, reproducible fixation stimulus. The fixation mark has a structure and a predominant direction which can be identified by the test subject only when the test subject has foveal fixation. This is achieved in that the fixation mark is formed, for example, as a Landolt ring which adopts discrete directional orientations when rotated. A Geneva drive generates the discrete directional orientations of the fixation mark from a uniform rotating movement in 90-degree rotations with a stationary interval. The test subject must constantly follow the slit of the Landolt ring during the examination, which can be accomplished only with corresponding foveal fixation.

The solutions mentioned above are provided predominantly for campimetric examination, i.e., for determining the visual field or defects in the visual field. The fixation marks used in treatment devices are generally stationary. Although laser treatments in ophthalmology last only minutes, unwanted eye movements nevertheless occur when using stationary fixation marks. Also, this cannot be prevented by alternating the type, color and/or intensity of the fixation marks.

OBJECT AND SUMMARY OF THE INVENTION

It is the primary object of the present invention to develop a solution which prevents or at least minimizes unwanted movements of an eye to be treated.

According to the invention, this object is met by a method for displaying a fixation mark for ophthalmologic treatment devices comprising the steps of projecting the fixation mark to be displayed in the field of the vision of the eye to be treated, allowing the patient to orient the eye to be treated on this fixation mark through foveal fixation and moving the fixation mark in the field of vision of the patient, wherein the movement is carried out in such a way that the patient can easily follow the fixation mark.

The proposed technical solution relates to a fixation object which can be used in ophthalmologic examination devices as well as in ophthalmologic treatment devices. By means of the moving fixation object, the patient's eye is oriented on the fixation object and easily follows it. Since the patient is occupied in following the fixation object with his/her eyes, the risk of glancing away is substantially reduced.

The invention will be described in the following with reference to an embodiment example.

DESCRIPTION OF THE PREFERRED EMBODIMENTS

In the proposed method for displaying a fixation mark for ophthalmologic treatment devices, the fixation mark to be displayed is projected in the field of vision of the eye to be treated so that the patient orients the eye to be treated on this fixation mark by foveal focusing. The fixation mark is moved in the field of vision of the patient and the movement is carried out in such a way that the patient can easily follow the fixation mark. The movement of the fixation mark in the field of vision of the patient is carried out continuously or discontinuously, according to a predetermined sequence, or randomly. In this way, no unwanted eye movements can take place.

Measurement or therapy can be carried out differently depending on the kind of movement of the fixation mark.

For example, when the fixation mark is moved discontinuously in the field of vision of the patient, diagnosis or therapy is preferably carried out only within the short stationary phases of the fixation mark. In contrast, when the fixation mark is moved continuously, diagnosis or therapy can also be carried out while the eye follows the movement of the fixation mark.

The fixation mark can be displayed and moved, for example, on a display or an XY mirror unit. The movement of the diagnostic beam or therapeutic beam should then be carried out by means of the same XY mirror unit or should be corrected by the movement of the fixation mark. For this purpose, it is advantageous when the movement of the fixation mark is carried out according to a predetermined sequence. A predetermined movement sequence can also be dynamically structured in a subjective manner for the patient so that there is no fatigue effect.

In principle, it is also possible to move the fixation mark randomly in the field of vision of the patient. In this case, for exact positioning and tracking of the diagnostic beam and therapeutic beam it is absolutely necessary to acquire the position of the fixation mark online, e.g., by means of an eye tracker, and to take into account the movement of the diagnostic beam or therapeutic beam simultaneously.

In another embodiment, the movement of the fixation mark can also be used to position the eye in a specific manner. The diagnostic beam or therapeutic beam remains rigid; the beam is positioned on the eye through the eye movement. For this purpose, it is necessary that the eye movement can track the moving fixation mark.

By the method according to the invention for displaying a fixation mark for ophthalmologic treatment devices, it can be ensured that unwanted and uncontrolled movements of the eye being treated do not occur during treatment.

While the foregoing description and drawings represent the present invention, it will be obvious to those skilled in the art that various changes may be made therein without departing from the true spirit and scope of the present invention.

What is claimed is:

1. A method of orienting the eye of a patient to help prevent the eye from moving in a manner that would interfere with treatment being carried out by an ophthalmologic treatment device, the method comprising the steps of:
    projecting a fixation mark to be displayed in the field of vision of the eye to be treated;
    allowing the patient to orient the eye to be treated on this fixation mark through foveal fixation; and
    moving the fixation mark in the field of vision of the patient during the treatment being carried out by the ophthalmologic treatment device;
    wherein the movement of the fixation mark is used to position the eye in a specific manner so that (a) the patient can easily follow the fixation mark and (b) the movement of the fixation mark makes the eye less likely to move in a manner that would interfere with the treatment being carried out by the ophthalmologic treatment device.

2. The method of orienting the eye of a patient according to claim 1;
    wherein the movement of the fixation mark in the field of vision of the patient is carried out continuously or discontinuously, according to a predetermined sequence, or randomly.

3. The method of orienting the eye of a patient according to claim 1;
    wherein the fixation mark is moved discontinuously in the field of vision of the patient, diagnosis or therapy being carried out only within short stationary phases of the fixation mark.

4. The method of orienting the eye of a patient according to claim 1;
    wherein the fixation mark is moved in the field of vision of the patient and a measurement is carried out while the eye follows the movement of the fixation mark.

5. The method of orienting the eye of a patient according to claim 1;
    wherein the movement of the fixation mark is carried out through variable projection on a stationary display.

6. The method of orienting the eye of a patient according to claim 1;
    wherein the movement of the fixation mark is carried out by an XY mirror unit.

7. The method of orienting the eye of a patient according to claim 1;
    wherein a movement of the fixation mark in the field of vision of the patient of a diagnostic beam or therapeutic beam is carried out by a XY mirror unit.

8. The method of orienting the eye of a patient according to claim 1;
    wherein a movement of a diagnostic beam or therapeutic beam is corrected by a predetermined movement of the fixation mark.

9. The method of orienting the eye of a patient according to claim 1;
    wherein a movement of a diagnostic beam or therapeutic beam is corrected by the movement of the fixation mark which is acquired online.

* * * * *